(12) United States Patent
Kearns (10) Patent No.: US 11,873,976 B1
(45) Date of Patent: Jan. 16, 2024

(54) BREATH SYNCHRONIZATION LIGHTING DEVICE

(71) Applicant: Michael Kearns, Sacramento, CA (US)

(72) Inventor: Michael Kearns, Sacramento, CA (US)

(*) Notice: Subject to any disclaimer, the term of this patent is extended or adjusted under 35 U.S.C. 154(b) by 0 days.

(21) Appl. No.: 17/808,644

(22) Filed: Jun. 24, 2022

(51) Int. Cl.
  *F21V 1/10* (2006.01)
  *A61M 21/02* (2006.01)
  *F21V 1/08* (2006.01)
  *H05B 47/165* (2020.01)

(52) U.S. Cl.
  CPC .............. *F21V 1/10* (2013.01); *A61M 21/02* (2013.01); *F21V 1/08* (2013.01); *H05B 47/165* (2020.01)

(58) Field of Classification Search
  CPC ...... A61N 5/06; A61N 5/0618; A61N 5/0613; A61N 2005/065; A61N 2005/0651; A61N 2005/0652; A61N 2005/0654; A61N 2005/0662; A61N 2005/0664; F21V 14/02–025; F21V 1/10; F21V 1/08; F21S 10/00; F21S 10/06–066; A61M 21/02
  See application file for complete search history.

(56) References Cited

U.S. PATENT DOCUMENTS

| | | | |
|---|---|---|---|
| 2,063,451 A | 12/1936 | Lunoe et al. | |
| 3,666,936 A | 5/1972 | Webster, Jr. et al. | |
| 3,790,772 A | 2/1974 | Newman et al. | |
| 4,591,955 A | 5/1986 | Kallay | |
| 5,749,646 A | 5/1998 | Brittell | |
| 7,708,423 B2 | 5/2010 | Hong | |
| 8,957,597 B2 | 2/2015 | Lin et al. | |
| 8,960,988 B2 | 2/2015 | Chien | |
| 9,163,799 B2 | 10/2015 | Chien | |
| 9,453,626 B2 | 9/2016 | Ruiz Bonet | |
| 9,532,745 B2 | 1/2017 | Jeanne | |
| 9,974,923 B2 | 5/2018 | Lapoint et al. | |
| 10,085,318 B2 | 9/2018 | Clout et al. | |
| 11,197,974 B2 | 12/2021 | Kremer et al. | |
| 2009/0190334 A1 | 7/2009 | Yang | |
| 2015/0131326 A1* | 5/2015 | Chien | F21S 10/00 362/221 |
| 2020/0215383 A1 | 7/2020 | Mankodi et al. | |

(Continued)

FOREIGN PATENT DOCUMENTS

| | | | | |
|---|---|---|---|---|
| CN | 210601415 U | 5/2020 | | |
| DE | 202008008899 U1 * | 4/2009 | .............. | F21S 6/002 |

OTHER PUBLICATIONS

Asim Ihsan, Healthy breathing with a smart bulb, Asim Ihsan's Meanderings, Aug. 13, 2020.

*Primary Examiner* — Anabel Ton
(74) *Attorney, Agent, or Firm* — Lewellyn Law, PLLC; Stephen Lewellyn (57) ABSTRACT

The breath synchronization lighting devices and apparatus helps the user to regulate their breathing rate by moving a light source with respect to a stationary shade or cover. The shade or cover, optionally perforated or with an integrated obscuring pattern, partially blocks the light created by the light source. The result is the generation of a shadow pattern on adjacent surfaces. As the light moves with respect to the cover, the shadow pattern correspondingly moves on the surface is surrounding the device. The result is a cycling shadow pattern on adjacent surfaces, the pattern timed to match the ideal breathing rate of the user, helping the user to slow their breathing and reach a calm and meditative state.

14 Claims, 11 Drawing Sheets

(56) References Cited

U.S. PATENT DOCUMENTS

| | | |
|---|---|---|
| 2020/0394885 A1 | 12/2020 | Nguyen et al. |
| 2021/0262626 A1 | 8/2021 | Chien |
| 2022/0357005 A1 | 11/2022 | Yeo et al. |
| 2023/0041557 A1* | 2/2023 | Lee .................... F21V 33/0004 |

* cited by examiner

BREATH SYNCHRONIZATION LIGHTING DEVICE

FIELD

This invention relates to the field of mood management devices and more particularly to a device that helps user reach a calm, meditative state.

BACKGROUND

Research has acknowledged the negative effect that psychological stress causes to the human body. Excessive stress is associated with physical and mental illnesses, including ulcers, heart attacks, depression, and anxiety, and a decrease of personal and professional productivity.

Given that stress is an ever-present part of daily living, the management, treatment, and reduction of stress is critical to mitigating its negative health effects.

Unhealthy means of managing stress are well-known, including substance abuse and eating disorders.

Clinically proven means of reducing stress include meditation and relaxation techniques, including controlled breathing exercises.

Given that each person has only a limited time to actively seek to reduce stress, increasing the efficiency of stress reduction makes it more likely that an individual will have an opportunity to reduce stress, and effectively reduce stress in less time.

What is needed is a device that will help a user reach a less stressful state—a meditative state or 'flow'—as efficiently as possible.

SUMMARY

The breath synchronization lighting devices and apparatus helps the user to regulate breathing rate by moving a light source with respect to a stationary shade or cover. The light source does not merely brighten and dim while remaining stationary, but moves, or appears to move, with respect to the shadow-generating cover.

The shade or cover, optionally perforated or with an integrated obscuring pattern, partially blocks the light created by the light source. The result is the generation of a shadow pattern on adjacent surfaces. As the light moves with respect to the cover, the shadow pattern correspondingly moves on the surfaces surrounding the device. The result is a cycling shadow pattern on adjacent surfaces, the pattern timed to match the ideal breathing rate of the user, helping the user to slow their breathing and reach a calm and meditative state.

The cycling or "breathing pattern" of the light can be at any speed or pattern but is preferably between two and sixteen cycles per minute. The preferred cycle rate is six cycles per minute. It can also produce asymmetrical patterns, for example 4 seconds of movement, 7 seconds of pause, and 8 seconds of movement.

In a first embodiment, the light source moves vertically within a lamp shade, or shadow-formation cover, that includes patterned cuts. The patterned cuts block light in a pattern, to create a shadow pattern on adjacent surfaces.

In an alternative embodiment, the shade moves vertically with respect to a stationary light, again resulting in a moving shadow pattern.

Multiple means of raising and lowering the light source exist.

For example, in the preferred embodiment the motion of a single light source may be replicated by a multiplicity of stationary individual light sources, each individual light source cycling between an on-state and an off-state. By cycling the light sources individually to create a rising and falling pattern, the physical motion of a single light source can be replicated without moving parts.

In an alternative embodiment slider-crank linkage, or cam-and-follower, can convert the rotational motion of a motor into linear motion of the light source.

Slider-crank linkage is a four-link mechanism with three pivot points and one sliding joint. Rotation of the crank causes linear motion of the slider, in turn moving a platform up and down or in and out.

This method of converting rotational motion into linear motion creates a natural pause at the top and bottom of the cycle, similar to the peak and valley of a sine wave, and imitates the natural breathing pattern of inhalation and exhalation.

The shade, perforated cover, or shadow-formation cover, can be created using a variety of methodologies. Materials include plastic, metal, paper, glass, ceramic, resin, and wood. The pattern that generates shadows can be created by casting, molding, or the removal of material by, for example, cutting holes, or by the addition of a light obscuring material within or on top of the shade, for example the application of paint or adhesive vinyl over a glass or acrylic shade.

Turning to operation, the device is preferably operated by integrated, onboard controls, or controlled remotely by, for example, a discrete remote or third-party control device, for example, a mobile phone.

In the preferred embodiment a color-changing light source is included to allow the user to select from a range of colors, or have the device alter color as it operates. Further optionally included is a dimming function, allowing the user to choose the brightness of the light based on the conditions present.

In other embodiments the light source has a color temperature in the white to yellow range.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Reference will now be made in detail to the presently preferred embodiments of the invention, examples of which are illustrated in the accompanying drawings. Throughout the following detailed description, the same reference numerals refer to the same elements in all figures.

Figure 1:
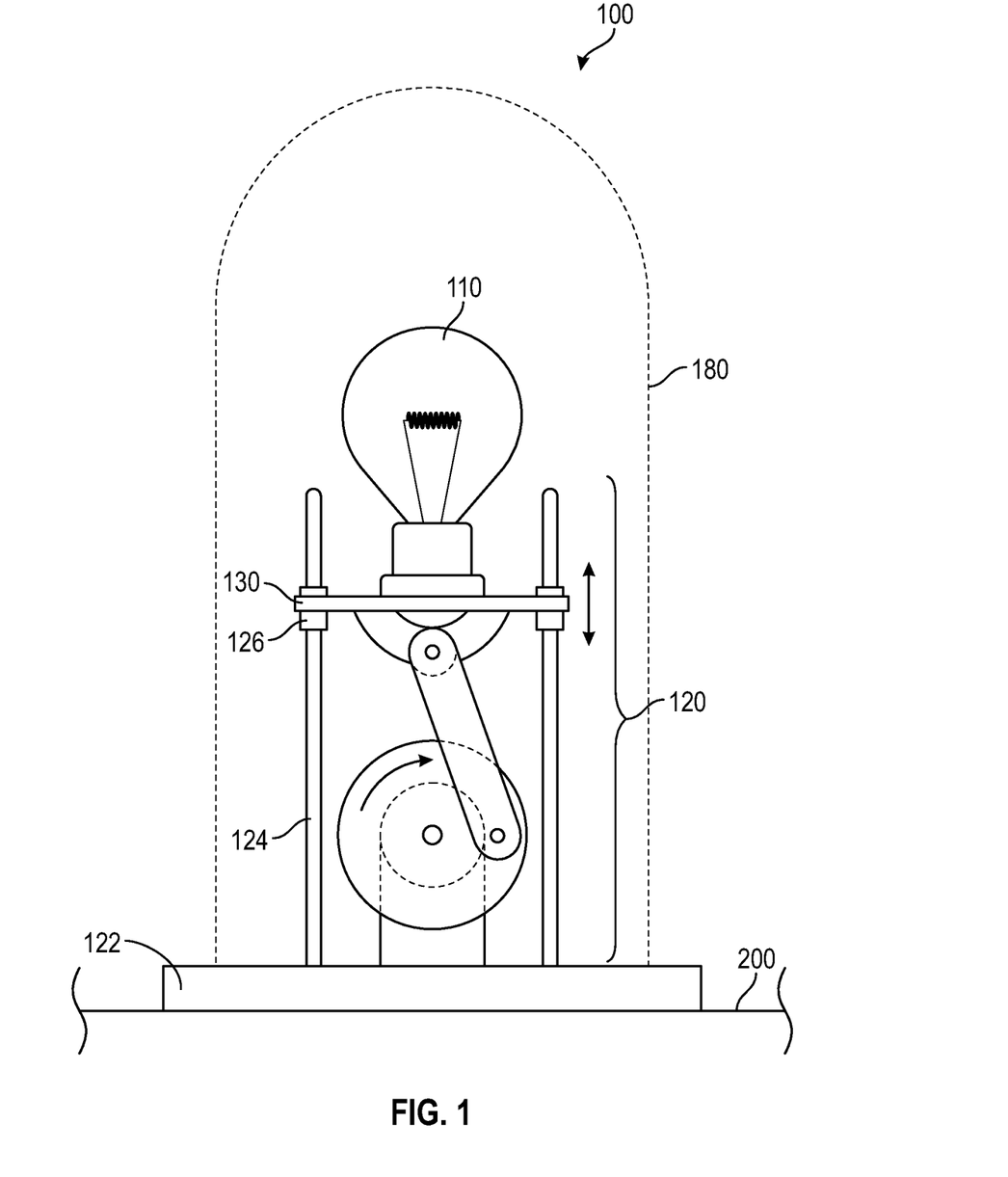
FIG. 1 illustrates a first view of a first embodiment of the breath synchronization lighting device.

Referring to FIG. 1, a first view of a first embodiment of the breath synchronization lighting device is shown.

The breath synchronization lighting device 100 includes a light source 110 that cycles between an upper position and a lower position inside a shadow-formation cover 180.

In the first embodiment, cycling is performed by a height adjustment mechanism 120. The height adjustment mechanism 120 includes a moving platform 130 that slides along guide rods 124, interfacing at guide bearings 126.

The height adjustment mechanism 120 is attached to a fixed platform 122, shown resting on a tabletop 200.

Figure 2:
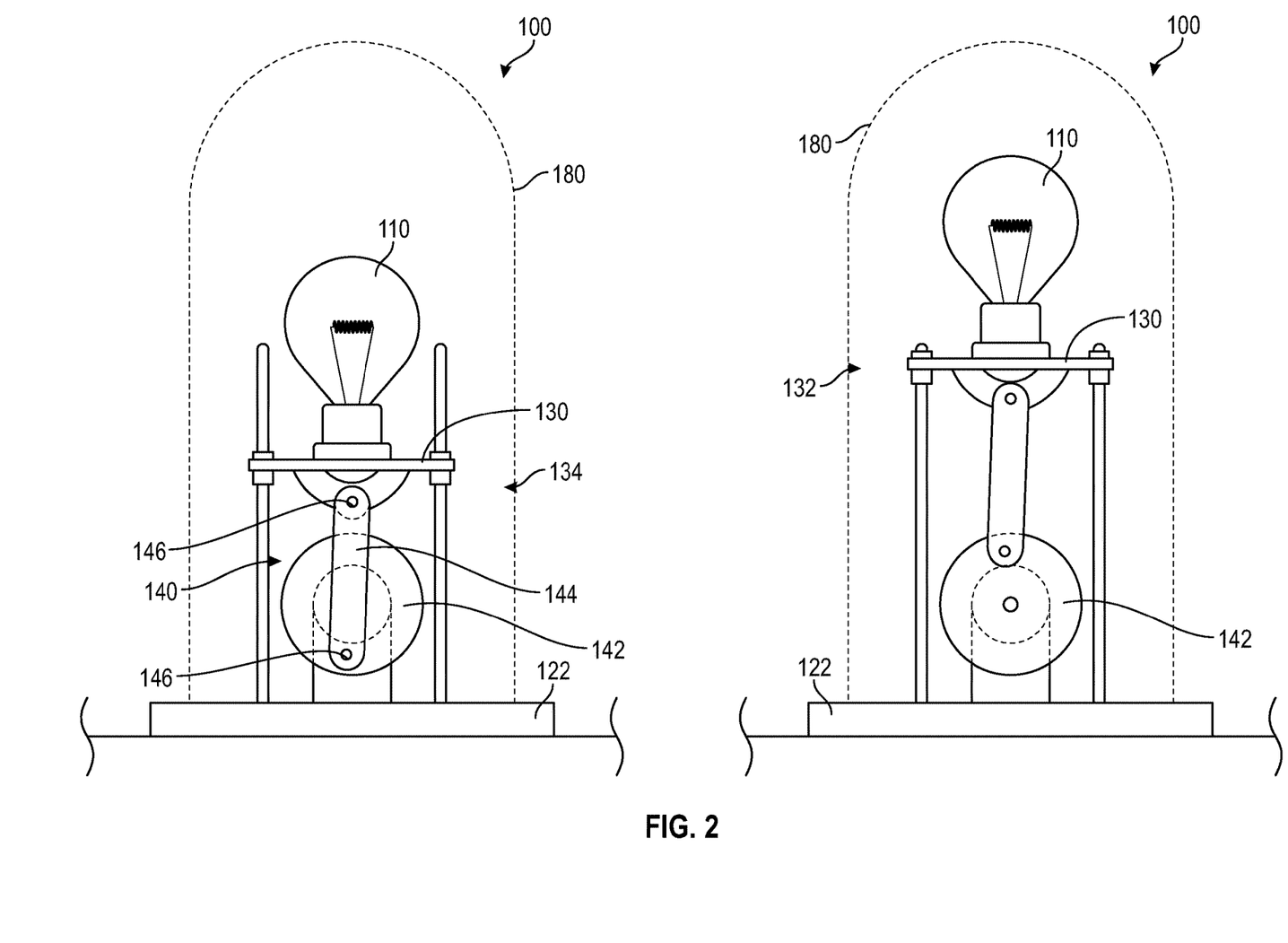
FIG. 2 illustrates a second view of the first embodiment, showing upper and lower positions of the breath synchronization lighting device.

Referring to FIG. 2, a second view of the first embodiment, showing upper and lower positions of the breath synchronization lighting device.

The light source 110 is shown at its lower position 134 in the left diagram, and its upper position 132 in the right diagram.

In the first embodiment, motion between these two positions is controlled by a slider-crank mechanism 140. The slider crank mechanism 140 includes a crank 142 that rotates, moving the arm 144 up and down, the arm connected to the crank 142 and moving platform 130 at pivot points 146.

When the crank 142 it is lowermost position, as shown in left diagram, the moving platform 130 is at its lower position 134.

When the crank 142 is at its uppermost position, as shown in the right diagram, the moving platform 130 is at its upper position 132.

Figure 3:
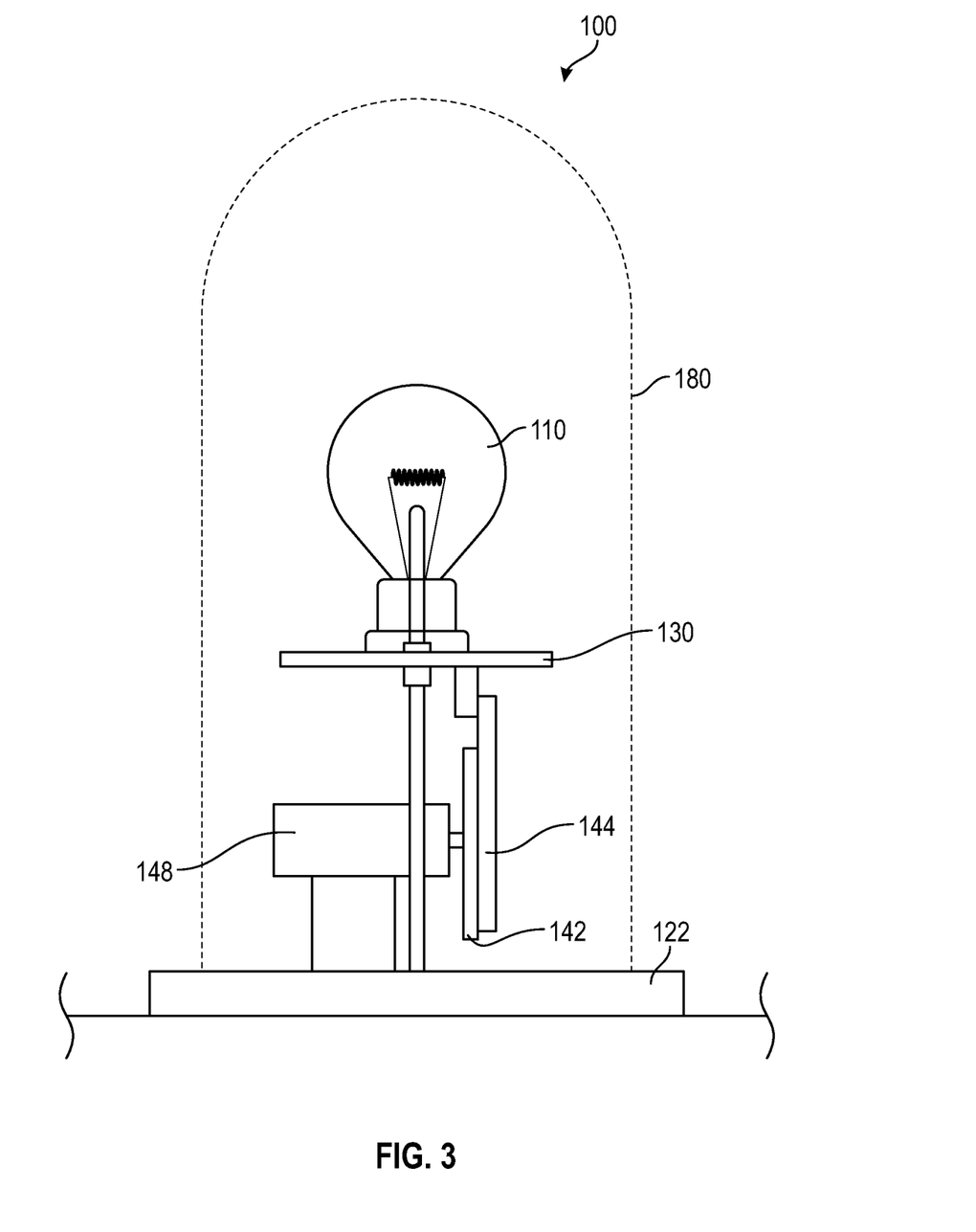
FIG. 3 illustrates a side view of the first embodiment of the breath synchronization lighting device.

Referring to FIG. 3, a side view of the first embodiment of the breath synchronization lighting device is shown.

The crank 142 is powered by a rotational motion source 148, for example an electric motor. Rotational motion source 148 rotates crank 142, moving arm 144, in turn causing cycling of moving platform 130.

As the light source no moves up and down inside the shadow-formation cover 180, a moving pattern of shadows is projected by the breath synchronization lighting device 100.

Figure 4:
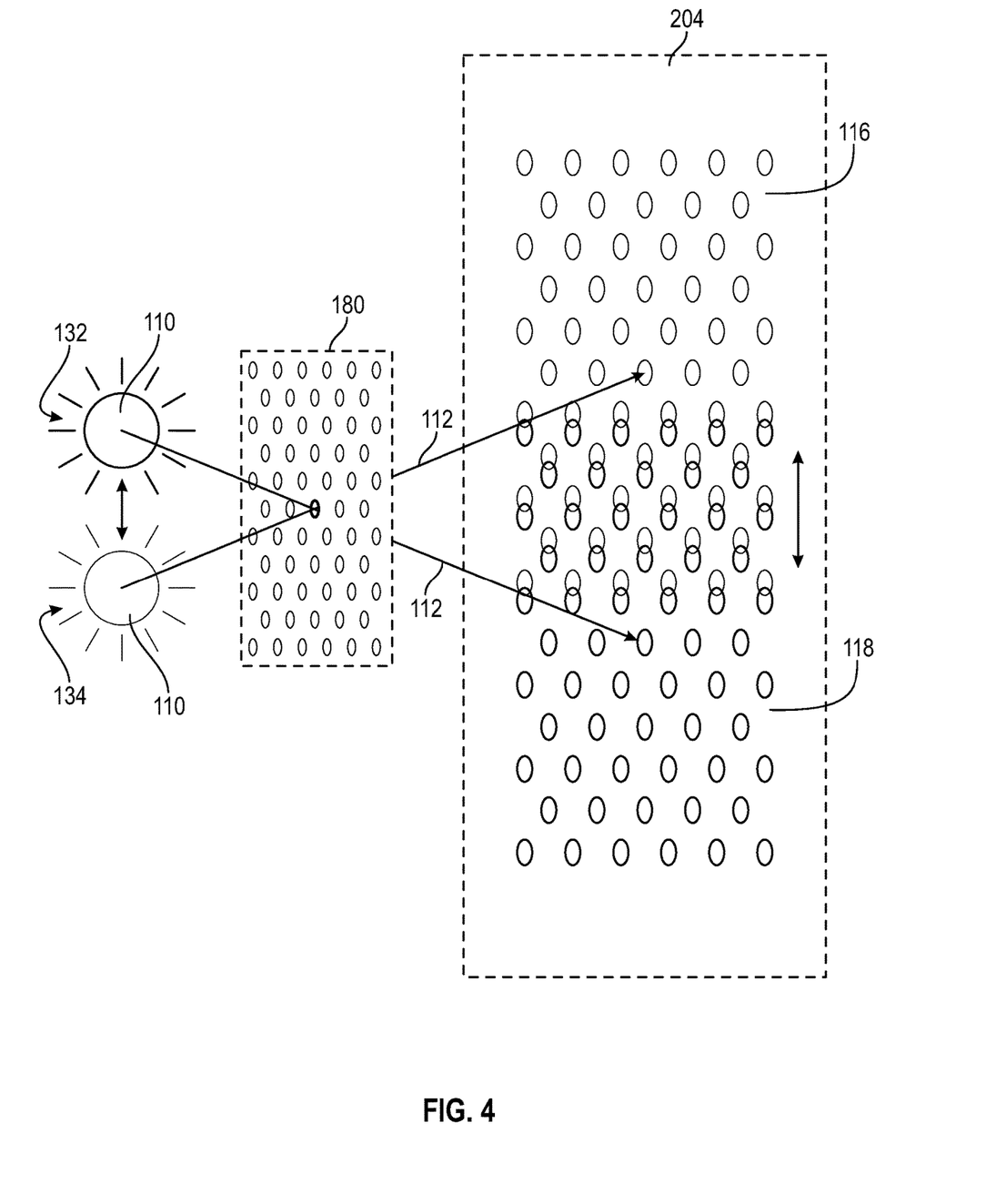
FIG. 4 illustrates a schematic view, showing the moving light and resulting moving shadow of the breath synchronization lighting device.

Referring to FIG. 4, a schematic view, showing the moving light and resulting moving shadow of the breath synchronization lighting device is shown.

The schematic shows the light source 110 at its upper position 132 and lower position 134. As the light 112 passes through the shadow-formation cover 180, a series of shadows is created on a wall 204. The upper position 132 of the light 110 creates the lower shadow pattern 118. The lower position 134 of the light source 110 creates the upper shadow pattern 116.

By cycling the light 110 between the upper position 132 and lower position 134, a rising and falling, raising and lowering, pattern of shadows is created.

Figure 5:
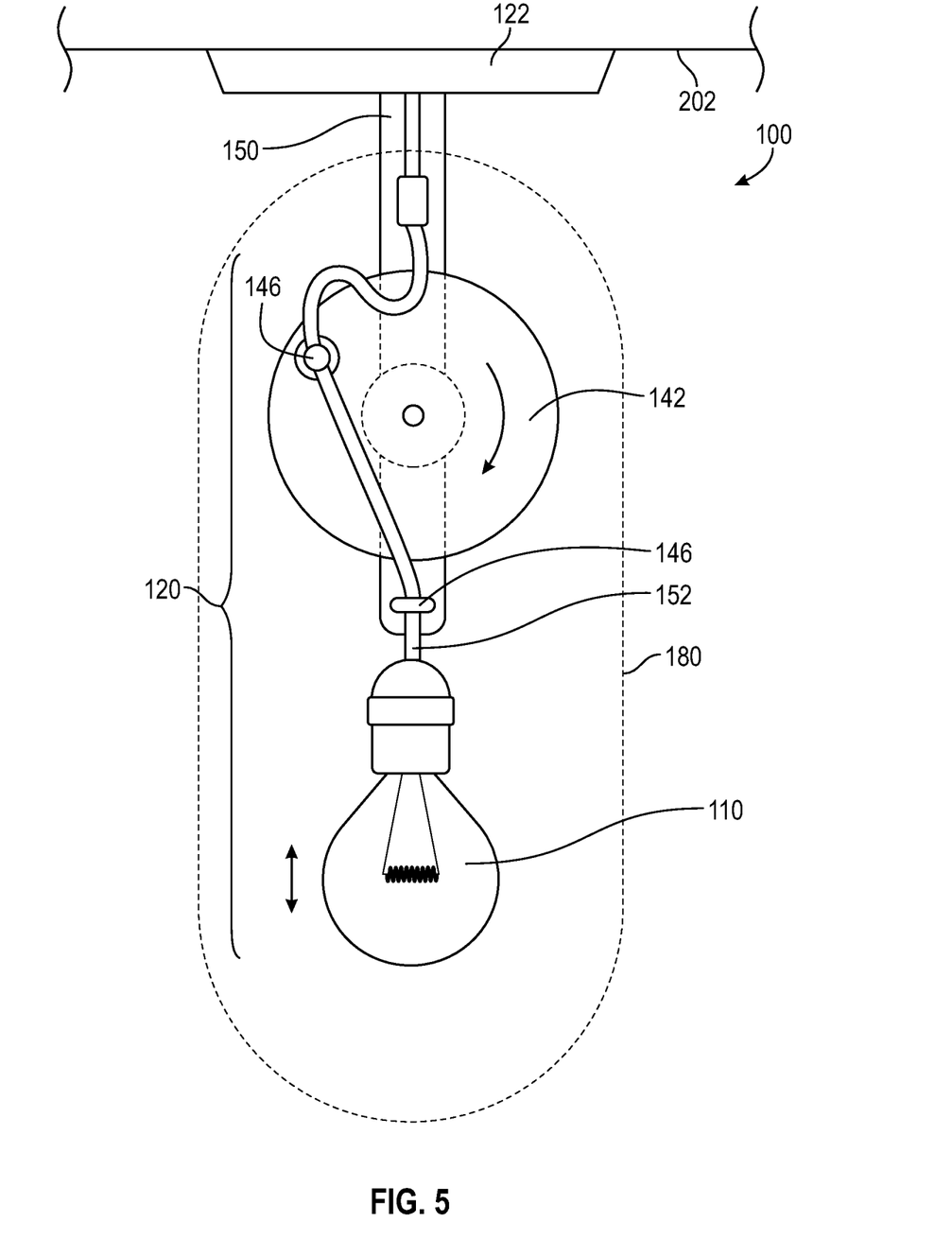
FIG. 5 illustrates a first view of a second embodiment of the breath synchronization lighting device.

Referring to FIG. 5, a first view of a second embodiment of the breath synchronization lighting device is shown.

In the second embodiment of the breath synchronization lighting device 100, the device is affixed to a ceiling 202 via a fixed platform 122.

Operation is similar to the first embodiment, with height adjustment mechanism 120 raising and lowering the light source 110 inside of the shadow-formation cover 180. The crank 142 rotates, raising and lowering the cord 152, the cord 152 passing through the pivot points 146. The entire height adjustment mechanism 120 is held up by a central support 150.

Figure 6:
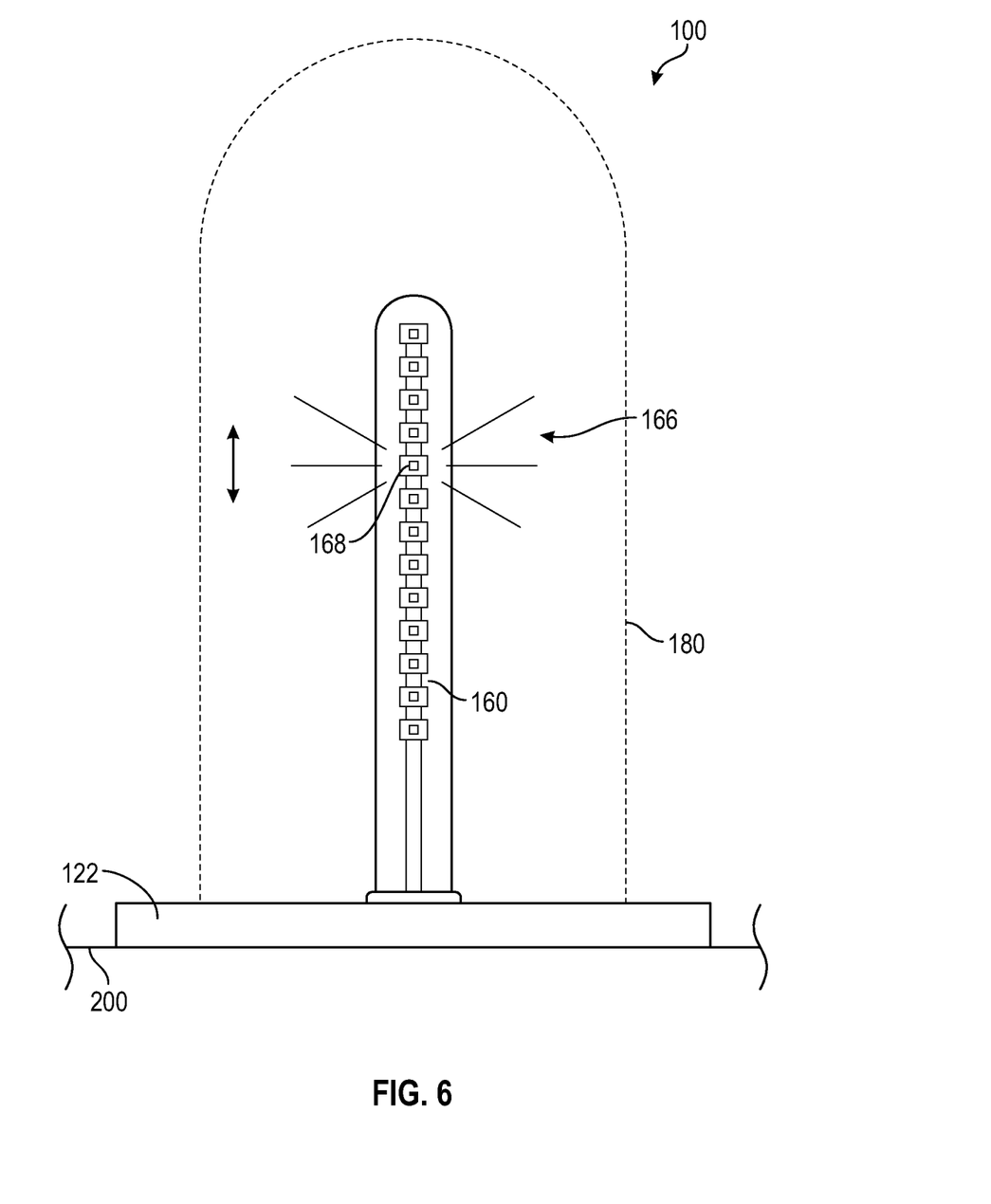
FIG. 6 illustrates a first view of a third embodiment of the breath synchronization lighting device.

Referring to FIG. 6, a first view of a third embodiment of the breath synchronization lighting device is shown.

In the third embodiment, the mechanical height adjustment mechanism has been replaced by a series of light sources 160.

The active light 168 of the series of light sources 160 moves up and down, simulating the physical motion of the light source 110 from the first and second embodiments (see FIGS. 1 through 5).

Figure 7:
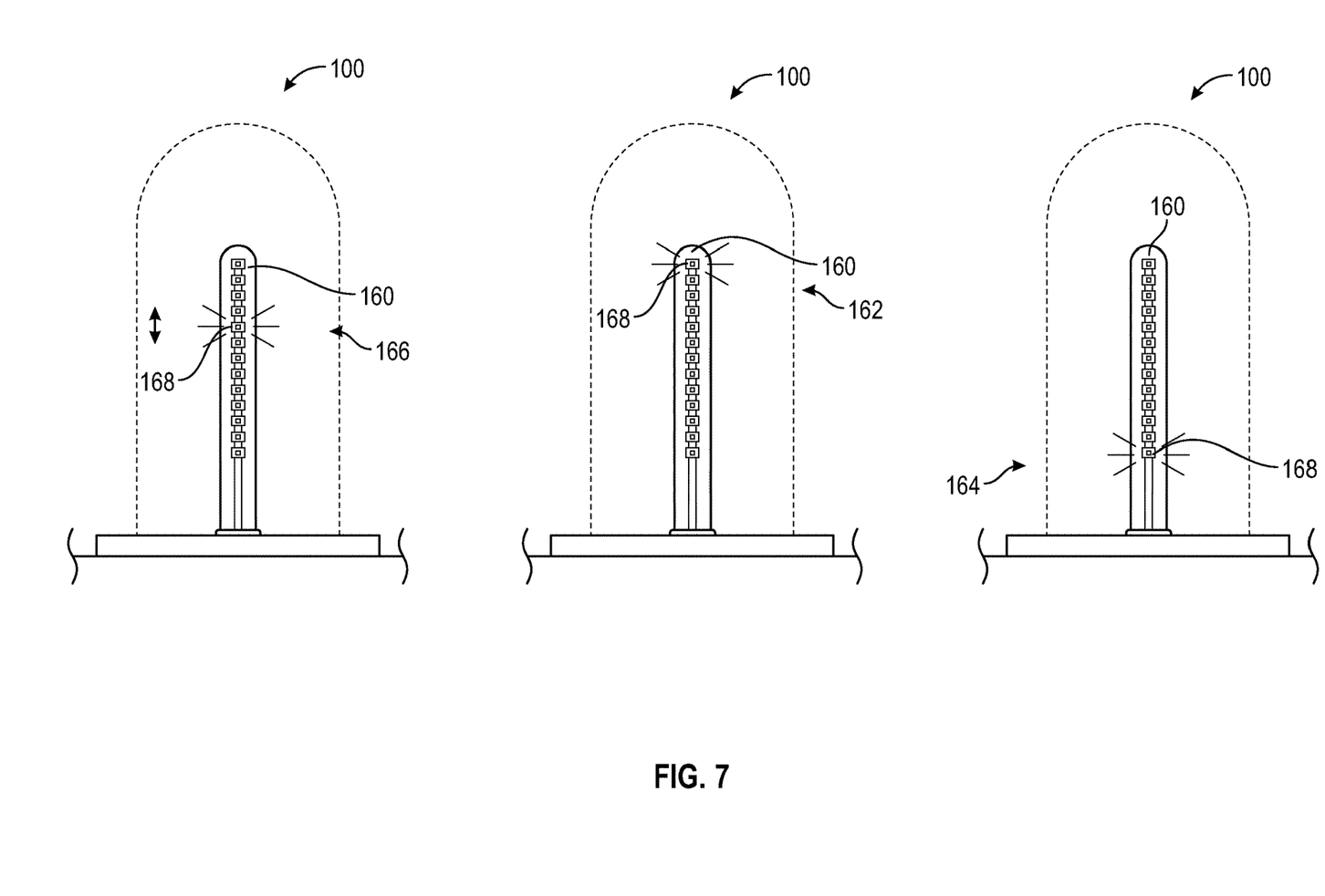
FIG. 7 illustrates a second view of the third embodiment, showing middle, upper, and lower positions of the breath synchronization lighting device.

Referring to FIG. 7, a second view of the third embodiment, showing middle, upper, and lower positions of the breath synchronization lighting device is shown.

The active light 168 moves between top position 162 and bottom position 164, passing through intermediate positions 166. The result is the simulation of a physical motion of light, creating a moving shadow pattern.

Figure 8:
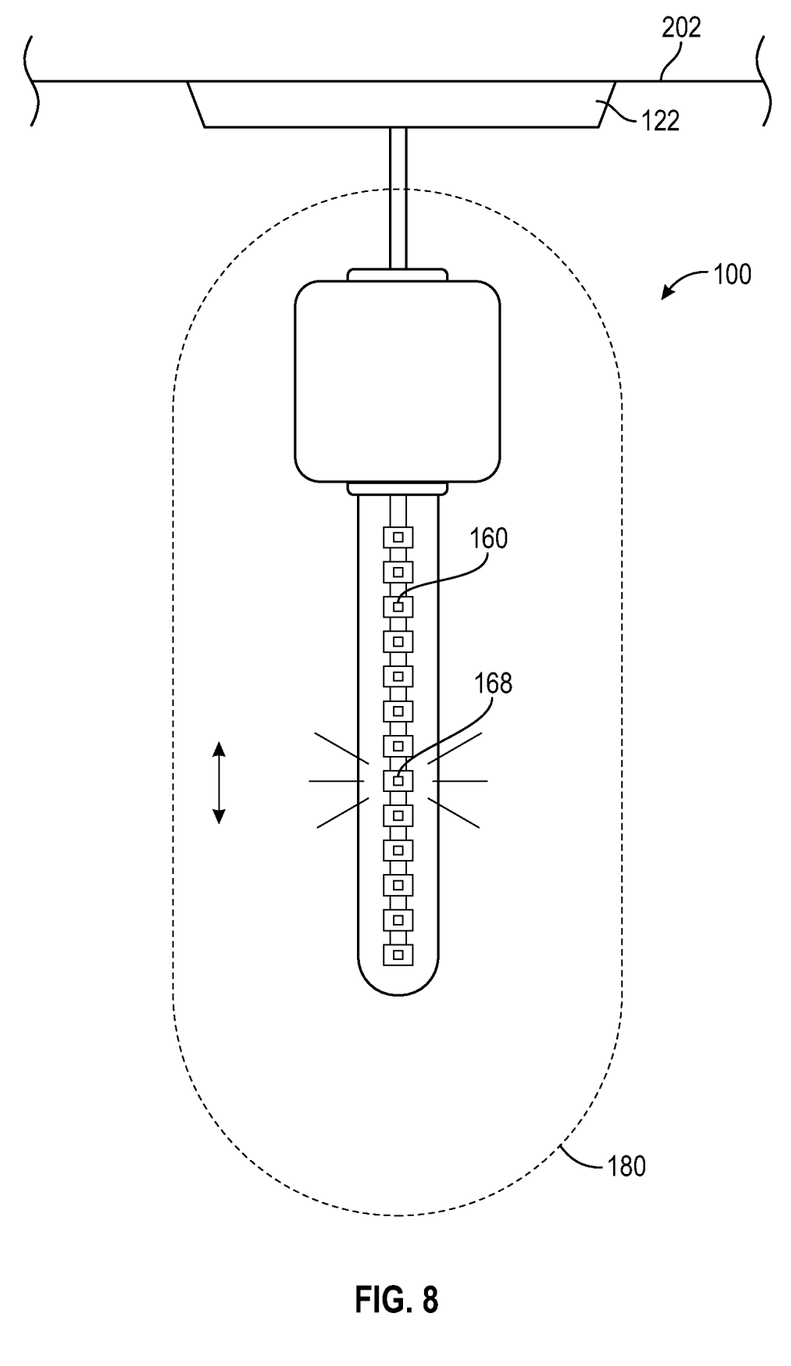
FIG. 8 illustrates a first view of a fourth embodiment of the breath synchronization lighting device.

Referring to FIG. 8, a first view of a fourth embodiment of the breath synchronization lighting device is shown.

The fourth embodiment of the breath synchronization lighting device 100 is inverted as compared to the third embodiment (see FIG. 7). The active light 168 moves along the series of light sources 160, the light passing through the shadow-formation cover 180 to create a moving shadow pattern.

Figure 9:
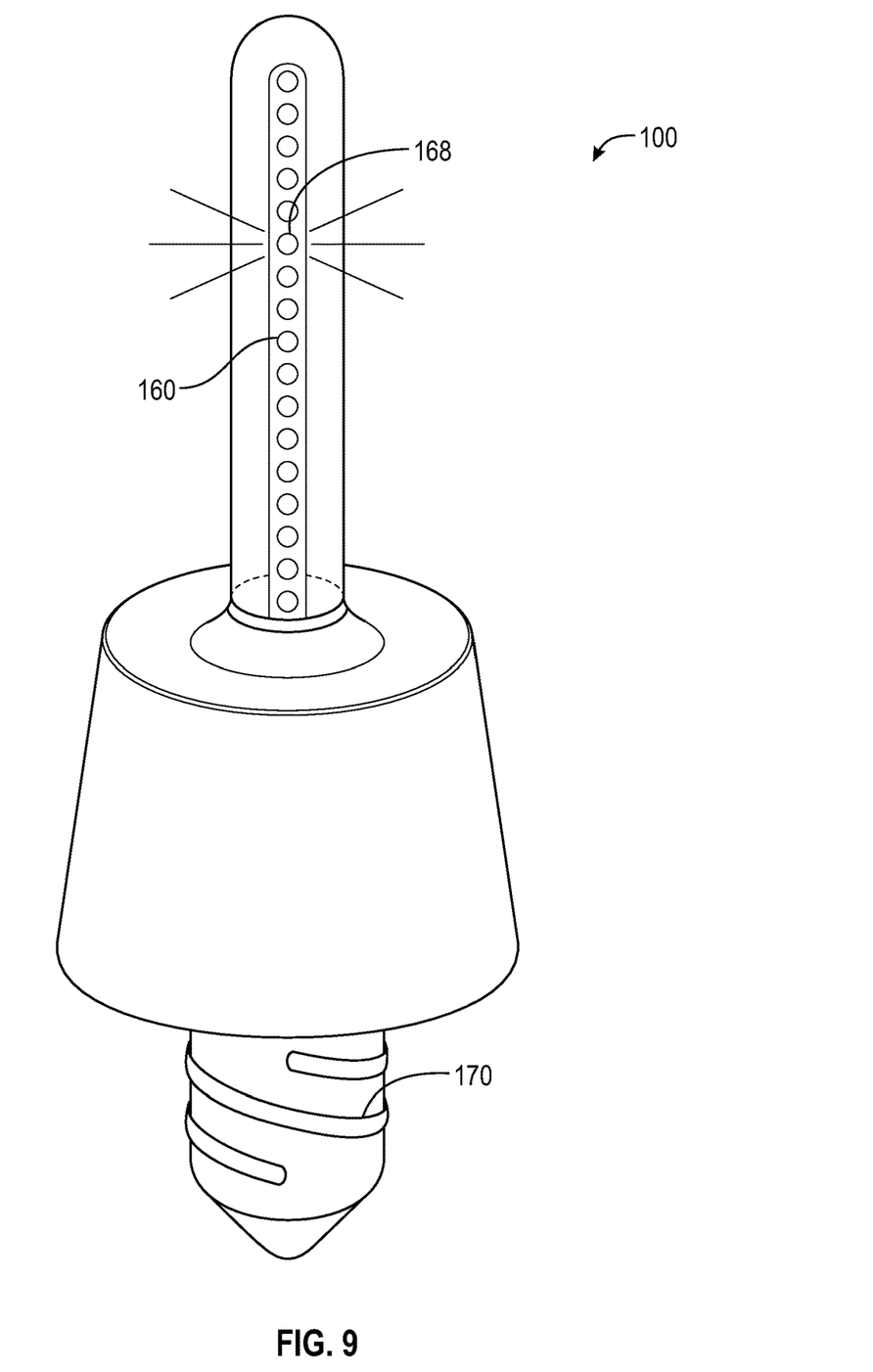
FIG. 9 illustrates a first view of a fifth embodiment of the breath synchronization lighting device.

Referring to FIG. 9, a first view of a fifth embodiment of the breath synchronization lighting device is shown.

The fifth embodiment of the breath synchronization lighting device 100 is intended for use in a standard incandescent light bulb socket. A series of light sources 160 interfaces with the socket via the base 170, the active light 168 moving along the series of light sources 160 to simulate a moving light source.

Figure 10:
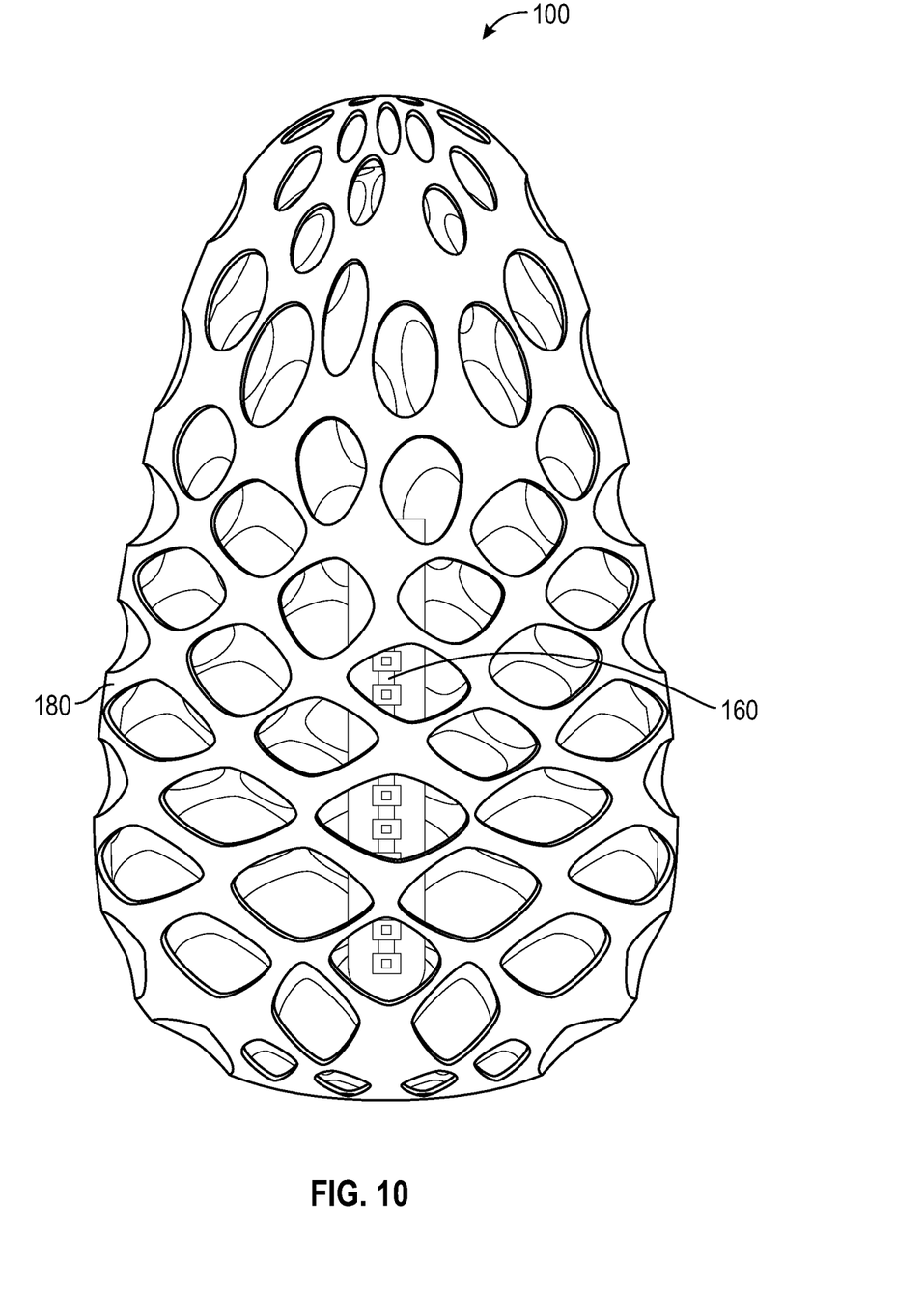
FIG. 10 illustrates a view of an example shadow-formation cover of the breath synchronization lighting device.

Referring to FIG. 10, a view of an example shadow-formation cover of the breath synchronization lighting device is shown.

A series of light sources with 6o is shown inside the shadow-formation cover 180. By virtue of the perforations, some light is allowed to pass through the shadow-formation cover 18o, whereas other light is blocked to create a shadow pattern.

Figure 11:
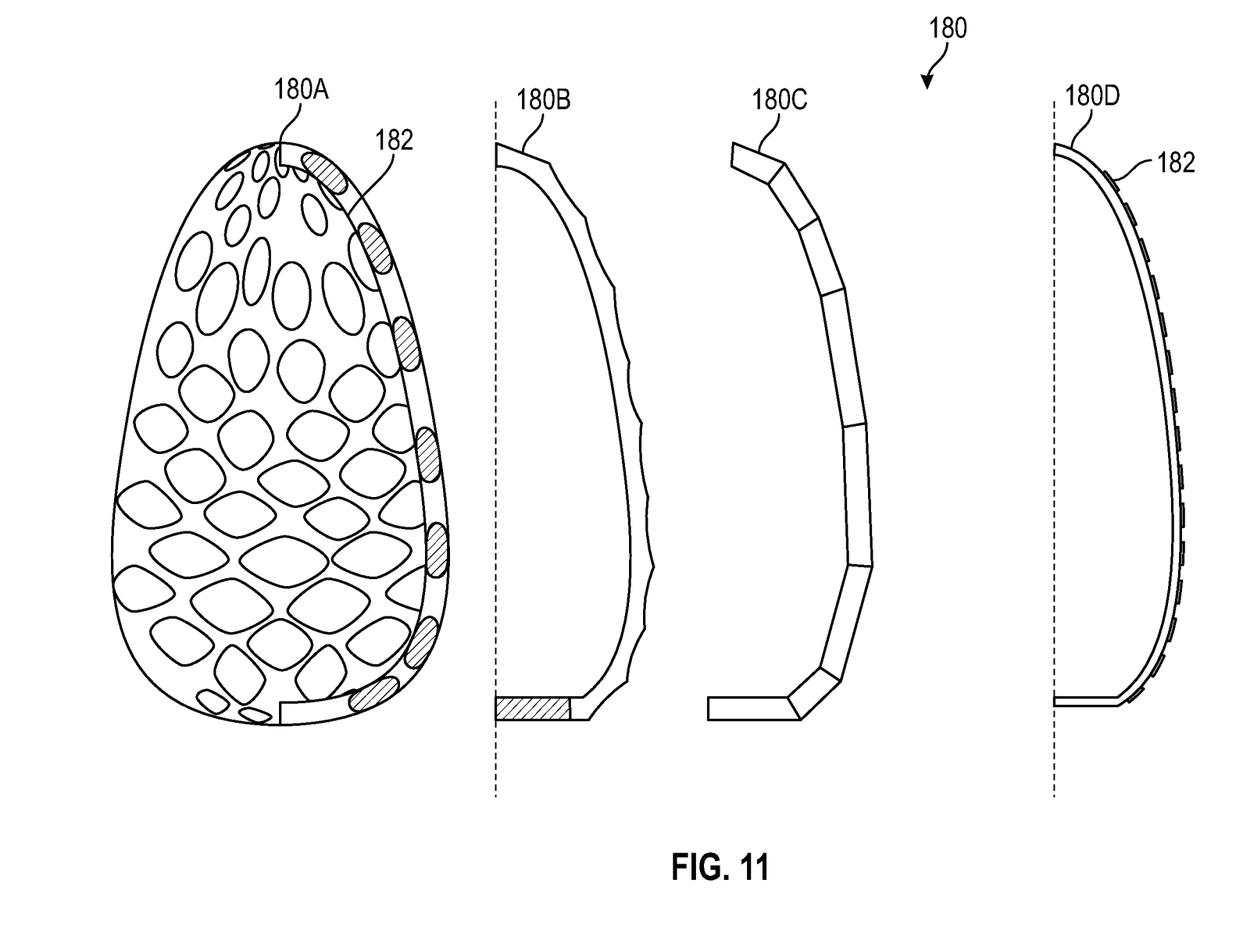
FIG. 11 illustrates cross sections of multiple examples of shadow-formation covers of the breath synchronization lighting device.

Referring to FIG. 11, cross sections of multiple examples of shadow-formation covers of the breath synchronization lighting device are shown.

The shadow-formation cover 180 comes in multiple embodiments. Shadow-formation cover 180A includes holes through which light can pass, the solid portions of the cover blocking light.

Shadow-formation cover 180B includes a scalloped or ridged outer surface outer surface, bending light as it passes through the cover.

Shadow formation cover 180C is formed from a series of flat faces, intentionally unevenly spreading the light as it passes through.

Shadow formation cover 180D is formed from a primarily clear material with an externally-applied light obscuring section 182 formed from, for example, vinyl stickers.

Shadow-formation covers 180 can be formed from a variety of materials, including plastic, acrylic, metal, paper, glass, ceramic, resin, and wood.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A device that creates a cycling pattern of shadows, the device comprising:
    a light source;
        the light source emitting light;
        the light source having an upper position, an intermediate position, and a lower position;
        the light source continuously cycling between the upper position and the lower position, passing through the intermediate position;
    a shadow-formation cover;
        the light from the light source passing through the shadow-formation cover;
        the shadow-formation cover obscuring or altering the light as it passes, creating a moving pattern of shadows on any adjacent surfaces; and
    whereby the moving pattern of shadows matches a desired breathing rate of a user, helping the user to reach a relaxed state.

2. The device of claim 1, further comprising:
   a height adjustment mechanism that includes:
        a moving platform that slides along a guide rod between a platform upper position and a platform lower position;
        the light source affixed to the moving platform; and
    whereby the height adjustment mechanism moves the light source up and down.

3. The device of claim 2, further comprising:
    a slider-crank mechanism formed from a crank affixed to an arm, the arm attaching to the moving platform at a pivot point; and
    rotation of the crank causing motion of the arm, the motion of the arm causing the moving platform to rise and fall.

4. The device of claim 1, wherein the light source is a series of light sources; and
    the series of light sources activating in series to create an appearance of a single moving light source by having an active light cycle between a top position and a bottom position.

5. A device to project a moving pattern of shadows onto adjacent surfaces, the device comprising:
    a light source that emits light;
    a shadow-forming cover adjacent to the light source;
    the light source cyclically changing position in a linear back-and-forth movement between an first light source position and a second light source position with respect to the shadow-forming cover;
    the light emitted by the light source being partially obscured by the shadow-forming cover, resulting in a cyclically changing shadow pattern projected on adjacent surfaces; and
    whereby the cyclically changing shadow pattern is timed to match a desired breathing rate of a user, helping the user to reach a meditative state.

6. The device of claim 5, wherein:
    the light source cyclically changes position vertically, cycling between the first light source position and the second light source position.

7. The device of claim 5, further comprising:
    a height adjustment mechanism that includes a moving platform that slides along a guide rod between a platform upper position and a platform lower position; and
    the light source affixed to the moving platform whereby the height adjustment mechanism moves the light source up and down.

8. The device of claim 7, further comprising:
    a slider-crank mechanism formed from a crank affixed to an arm, the arm attaching to the moving platform at a pivot point; and
    rotation of the crank causing motion of the arm, the motion of the arm causing the moving platform to rise and fall.

9. The device of claim 5, wherein the light source is a series of light sources; and
    the series of light sources activating in series to create an appearance of a single moving light source by having an active light cycle between the first light source position and the second light source position.

10. A device to create a cyclically moving pattern of shadows on adjacent surfaces, the cyclically moving pattern of shadows created by motion of a shade and a light with respect to each other, the device comprising:
    a perforated cover;
    a light source;
    the light source creating light, the light passing through the perforated cover;
    the perforated cover partially blocking the light to create a pattern of light and shadow on adjacent surfaces;
    the pattern of light and shadow cycling as the light source moves cyclically in a linear back-and-forth movement between an first light source position and a second light source position with respect to the perforated cover;
    whereby the pattern of light and shadow moves in a manner that encourages a user to match their breathing rate, helping the user to reach a calm state.

11. The device of claim 10, wherein:
    the light source cyclically changes position vertically, cycling between the first light source position and the second light source position.

12. The device of claim 10, further comprising:
    a height adjustment mechanism that includes:
    a moving platform that slides along a guide rod between a platform upper position and a platform lower position;
    the light source affixed to the moving platform; and
    whereby the height adjustment mechanism moves the light source up and down.

13. The device of claim 11, further comprising:
    a slider-crank mechanism formed from a crank affixed to an arm, the arm attaching to a moving platform at a pivot point;

rotation of the crank causing motion of the arm, the motion of the arm causing the moving platform to rise and fall; and the light source is affixed to the moving platform.

14. The device of claim 10, wherein:

the light source is a series of light sources; and the series of light sources activating in series to create an appearance of a single moving light source by having an active light cycle between the first light source position and the second light source position.

* * * * *